United States Patent [19]
Parodi

[11] Patent Number: 5,591,229
[45] Date of Patent: Jan. 7, 1997

[54] AORTIC GRAFT FOR REPAIRING AN ABDOMINAL AORTIC ANEURYSM

[76] Inventor: Juan C. Parodi, Mercedes 4255, Buenos Aires, Argentina, 1419

[21] Appl. No.: 466,356

[22] Filed: Jun. 6, 1995

Related U.S. Application Data

[60] Division of Ser. No. 130,352, Oct. 1, 1993, which is a continuation-in-part of Ser. No. 535,745, Jun. 11, 1990, Pat. No. 5,360,443.

[51] Int. Cl.$^6$ .............................. A61F 2/06; A61M 29/00
[52] U.S. Cl. .................................. 623/1; 623/12; 606/195
[58] Field of Search .................................. 623/1, 11, 12; 606/194, 195, 191, 198

[56] References Cited

U.S. PATENT DOCUMENTS

| | | | |
|---|---|---|---|
| 3,657,744 | 4/1972 | Ersek | 623/12 |
| 4,577,631 | 3/1986 | Kreamer | 128/334 |
| 4,776,337 | 10/1988 | Palmaz | 128/343 |
| 4,932,956 | 6/1990 | Reddy et al. | 606/192 |
| 5,024,658 | 6/1991 | Kozlov et al. | 604/96 |
| 5,061,275 | 11/1991 | Wallsten | |
| 5,078,726 | 4/1992 | Kreamer | 606/194 |
| 5,219,355 | 6/1993 | Parodi et al. | 606/191 |
| 5,316,023 | 5/1994 | Palmaz et al. | 128/898 |
| 5,360,443 | 11/1994 | Barone | 623/1 |

FOREIGN PATENT DOCUMENTS 92309777 10/1992 European Pat. Off. .

OTHER PUBLICATIONS

"Transfemoral Intraluminal Graft Implantation for Abdominal Aortic Aneurysms"; Parodi et al.; Annals of Vascular Surgery; vol. 5–No. 6, 1991.

"Transfemoral Placement of Intraluminal Polyurethane Prosthosis for Abdominal Aortic Aneurysm"; Balko et al; Journal of Surgical Research 40 (1986).

"Self–Expanding Endovascular Graft", Yoshioka et al, American Journal of Radiology: 151; Oct. 1988.

From Advances in Vascular Surgery, vol. 1, 1993, Mosby–Year Book Inc., Chapters entitled "Enoovascular Repair of Abdominal Aortic Aneurysms", pp. 85–106, by Juan C. Parodi and Intravascular Stents, pp. 107–135, by Julio C. Palmaz, Frank J. Rivora, and Carlos Excarnacion.

*Primary Examiner*—Debra S. Brittingham
*Attorney, Agent, or Firm*—Ben D. Tobor

[57] ABSTRACT

An aortic graft for intraluminal delivery to repair an abdominal aortic aneurysm is provided with at least one wire which is woven into the distal, or lower, end of the graft, which wire permits the distal end of the graft to conform to, and sealingly engage, within the aortic bifurcation region of the aneurysm.

9 Claims, 9 Drawing Sheets

AORTIC GRAFT FOR REPAIRING AN ABDOMINAL AORTIC ANEURYSM

RELATED APPLICATION

This application is a division of Ser. No. 08/130,352, filed Oct. 1, 1993, continuation-in-part application of application Ser. No. 07/535,745, filed Jun. 11, 1990, and entitled "Aortic Graft, and Method and Apparatus for Repairing an Abdominal Aortic Aneurysm, now U.S. Pat. No. 5,360,443.

BACKGROUND OF THE INVENTION

1. Field of the Invention

The invention relates to an aortic graft for intraluminal delivery, and a method and apparatus for repairing an abdominal aortic aneurysm.

2. Description of the Prior Art

An abdominal aortic aneurysm is a sac caused by an abnormal dilation of the wall of the aorta, a major artery of the body, as it passes through the abdomen. The abdomen is that portion of the body which lies between the thorax and the pelvis. It contains a cavity, known as the abdominal cavity, separated by the diaphragm from the thoracic cavity and lined with a serous membrane, the peritoneum. The aorta is the main trunk, or artery, from which the systemic arterial system proceeds. It arises from the left ventricle of the heart, passes upward, bends over and passes down through the thorax and through the abdomen to about the level of the fourth lumbar vertebra, where it divides into the two common iliac arteries.

The aneurysm usually arises in the infrarenal portion of the arterioscleroticly diseased aorta, for example, below the kidneys, When left untreated, the aneurysm will eventually cause rupture of the sac with ensuing fatal hemorrhaging in a very short time. High mortality associated with the rupture has led to the present state of the art and the transabdominal surgical repair of abdominal aortic aneurysms. Surgery involving the abdominal wall, however, is a major undertaking with associated high risks. There is considerable mortality and morbidity associated with this magnitude of surgical intervention, which in essence involves replacing the diseased and aneurysmal segment of blood vessel with a prosthetic device which typically is a synthetic tube, or graft, usually fabricated of either DACRON®, TEFLON®, or other suitable material.

To perform the surgical procedure, requires exposure of the aorta through an abdominal incision which can extend from the rib cage to the pubis. The aorta must be closed both above and below the aneurysm, so that the aneurysm can then be opened and the thrombus, or blood clot, and arteriosclerotic debris removed. Small arterial branches from the back wall of the aorta are tied off. The DACRON® tube, or graft, of approximately the same size of the normal aorta is sutured in place, thereby replacing the aneurysm. Blood flow is then reestablished through the graft. It is necessary to move the intestines in order to get to the back wall of the abdomen prior to clamping off the aorta.

If the surgery is performed prior to rupturing of the abdominal aortic aneurysm, the survival rate of treated patients is markedly higher than if the surgery is performed after the aneurysm ruptures, although the mortality rate is still quite high. If the surgery is performed prior to the aneurysm rupturing, the mortality rate is typically slightly less than 10%. Conventional surgery performed after the rupture of the aneurysm is significantly higher, one study reporting a mortality rate of 66.7%. Although abdominal aortic aneurysms can be detected from routine examinations, the patient does not experience any pain from the condition. Thus, if the patient is not receiving routine examinations, it is possible that the aneurysm will progress to the rupture stage, wherein the mortality rates are significantly higher.

Disadvantages associated with the conventional, prior art surgery, in addition to the high mortality rate are: the extended recovery period associated with such surgery; difficulties in suturing the graft, or tube, to the aorta; the loss of the existing aorta wall and thrombosis to support and reinforce the graft; the unsuitability of the surgery for many patients having abdominal aortic aneurysms; and the problems associated with performing the surgery on an emergency basis after the aneurysm has ruptured. As to the extent of recovery, a patient can expect to spend from 1 to 2 weeks in the hospital after the surgery, a major portion of which is spent in the intensive care unit, and a convalescence period at home from 2 to 3 months, particularly if the patient has other illness such as heart, lung, liver, and/or kidney disease, in which case the hospital stay is also lengthened. Since the graft must be secured, or sutured, to the remaining portion of the aorta, it is many times difficult to perform the suturing step because of thrombosis present on the remaining portion of the aorta, and that remaining portion of the aorta wall may many times be friable, or easily crumbled.

Since the aneurysm is totally removed in the prior art surgery, the new graft does not have the benefit of the previously existing aortic wall, and the thrombosis therein, which could be utilized to support and reinforce the graft were the graft to be able to be inserted within the existing aortic wall and thrombosis. Since many patients having abdominal aortic aneurysms have other chronic illnesses, such as heart, lung, liver, and/or kidney disease, coupled with the fact that many of these patients are older, the average age being approximately 67 years old, these patients are not ideal candidates for such surgery, which is considered major surgery. Such patients have difficulties in surviving the operation. Lastly, once the aneurysm has ruptured, it is difficult to perform a conventional surgery on an expedited basis because of the extent of the surgery.

Accordingly, prior to the development of the present invention, there has been no graft for intraluminal delivery, or method and apparatus for repairing an abdominal aortic aneurysm, which: does not have a high mortality rate; does not have an extended recovery period; does not require suturing the graft to the remaining aorta wall; permits the existing aortic wall and thrombosis therein to support and reinforce the graft; is suitable for patients with other chronic illnesses; and is more readily performed on an emergency basis after rupture of the aneurysm. Therefore, the art has sought an aortic graft for intraluminal delivery, and a method and apparatus for repairing an abdominal aortic aneurysm which is believed to: not have a high mortality rate; not require an extended recovery period; not require suturing the graft to the remaining aortic wall: permit the existing aortic wall and thrombosis therein to be retained to reinforce and support the aortic graft; be suitable for patients having other chronic illnesses; and be more readily, quickly performed on an emergency basis after rupture of the aneurysm.

SUMMARY OF THE INVENTION

In accordance with the invention, the foregoing advantages have been achieved through the present aortic graft for intraluminal delivery to repair an abdominal aortic aneurysm in an aorta having two iliac arteries associated therewith at an aortic bifurcation. The present invention includes: a tube having first and second ends and a wall surface disposed between the two ends, at least a portion of the tube adapted to be disposed within the abdominal aortic aneurysm; a first means for securing the first end of the tube to the aorta, the first securing means having a first diameter which permits intraluminal delivery of the first securing means into the aorta and the first securing means having a second, expanded diameter, to secure the first end of the tube to the aorta; and a second means for securing the second end of the tube within the aortic bifurcation.

A further feature of the present invention is that the second means for securing the second end may include a thin-walled tubular member having a longitudinal axis, an interior, first and second ends, and a smooth outer tubular member wall surface disposed between the first and second ends, the tubular member wall surface having a substantially uniform thickness and a plurality of slots formed therein, the slots being disposed substantially parallel to the longitudinal axis of the tubular member, the second end of the tube being secured to the first end of the tubular member; the tubular member having a first diameter which permits intraluminal delivery of the tubular member into the aorta and the tubular member having a second, expanded and deformed diameter, upon an application from the interior of the tubular member of a radially, outwardly extending force, which second diameter is variable and dependent upon the force applied to the tubular member, whereby the tubular member may be expanded and deformed to secure the second end of the within the aortic bifurcation.

In accordance with the invention the foregoing advantages have also been achieved through the present aortic graft for intraluminal delivery to repair an abdominal aortic aneurysm in an aorta having two iliac arteries associated therewith at an aortic bifurcation having an interior surface. This aspect of the present invention includes: a tube having first and second ends and a wall surface disposed between the two ends, at least a portion of the tube adapted to be disposed within the abdominal aortic aneurysm; means for securing the first end of the tube to the aorta, the securing means having a first diameter which permits intraluminal delivery of the securing means into the aorta and the securing means having a second, expanded diameter, to secure the first end of the tube to the aorta; and a means for sealing the second end of the tube within the aorta bifurcation.

A further feature of this aspect of the present invention is that the means for sealing the second end of the tube may be at least one wire associated with the second end of the tube, the wire in the second end of the tube having a first cross-sectional configuration which permits intraluminal delivery of the tube and the means for sealing within the aortic bifurcation; and a second enlarged cross-sectional configuration, wherein the wire and second end of the tube conform to, and sealingly engage, the interior surface of the aortic bifurcation. An additional feature of the present invention is that the at least one wire may be associated with the second end of the tube by weaving the at least one wire into the second end of the tube, and the at least one wire may be woven into the second end of the tube in a generally zigzag pattern. A further feature of the present invention is that portions of the at least one wire may be woven into the second end of the tube with portions of the at least one wire extending outwardly, or inwardly, of the second end of the tube.

In accordance with the invention, the foregoing advantages have also been achieved through the present method for repairing an abdominal aortic aneurysm in an aorta having two iliac arteries associated therewith at an aortic bifurcation having an interior surface. The method of the present invention comprises the steps of: connecting an upper end of a tube to an expandable tubular member; disposing the tube and tubular member upon a first catheter having a first expandable, inflatable portion with the tubular member disposed upon the expandable, inflatable portion; intraluminally delivering the tube, tubular member and first catheter to the aorta and disposing at least a portion of the tube within the abdominal aortic aneurysm; expanding the first expandable, inflatable portion of the catheter to expand the tubular member to force the tubular member radially outwardly into contact with the aorta to secure the tubular member and at least a portion of the tube within the aorta; and securing a lower end of the tube within the aortic bifurcation whereby the tube provides a fluid passageway through the abdominal aortic aneurysm.

Another feature of the present invention is that the lower end of the tube may be secured within the aortic bifurcation by connecting the lower end of the tube to an expandable and deformable tubular member, which is forced radially outwardly into contact with the interior surface of the aortic bifurcation, and the expandable and deformable tubular member is forced radially outwardly by expanding a second expandable, inflatable portion of the first catheter to expand and deform the expandable and deformable tubular member. A further feature of the present invention is that the lower end of the tube may be secured within the aortic bifurcation by disposing an expandable and deformable tubular member within the lower end of the tube, which is forced radially outwardly into contact with the interior surface of the aortic bifurcation by expanding an expandable, inflatable portion of a second catheter to expand and deform the expandable and deformable tubular member.

In accordance with another aspect of the present invention, the foregoing advantages have been achieved through a method for repairing an abdominal aortic aneurysm in an aorta having two iliac arteries associated therewith at an aortic bifurcation having an interior surface. This aspect of the present invention includes the steps of: connecting an upper end of a tube to an expandable, tubular member; disposing the tube and tubular member upon a catheter having a first expandable, inflatable portion with the tubular member disposed upon the first expandable, inflatable portion; intraluminally delivering the tube, tubular member and catheter to the aorta and disposing at least a portion of the tube within the abdominal aortic aneurysm; expanding the first expandable, inflatable portion of the catheter to expand the tubular member to force the tubular member radially outwardly into contact with the aorta to secure the tubular member and at least a portion of the tube within the aorta; and sealing the second end of the tube within the aortic bifurcation, whereby the tube provides a fluid passageway through the abdominal aortic aneurysm.

Another feature of this aspect of the present invention is that the second end of the tube may be sealed within the aortic bifurcation by associating at least one wire with the lower end of the tube, and forcing the at least one wire and lower end of the tube outwardly to conform to, and sealingly engage against, the interior surface of the aortic bifurcation. An additional feature of this aspect of the present invention includes the step of weaving the at least one wire into the lower end of the tube, and the at least one wire may be woven in a generally zigzag pattern. A further feature of the present invention may include the step of weaving the at least one wire into the lower end of the tube with portions of the at least one wire extending outwardly, or inwardly, of the lower end of the tube.

Another aspect of the present invention is a balloon device for use in repairing an abdominal aortic aneurysm in an aorta having two iliac arteries associated therewith at an aortic bifurcation. This aspect of the present invention includes: a catheter having a longitudinal axis and at least three internal passageways; first and second inflatable balloons disposed upon the catheter and separated by a predetermined distance, each balloon connected to at least one of the internal passageways, the second balloon having first and second ends and a longitudinal axis which is substantially parallel to the longitudinal axis of the catheter, the first end of the second balloon being disposed closer to the first balloon then the second end of the second balloon; the first and second balloons having a generally cylindrical cross-sectional configuration upon being inflated, defined by an outer wall surface; and the second end of the second balloon including an end wall surface which is disposed substantially perpendicular to the longitudinal axis of a first portion of catheter disposed within the second balloon and substantially perpendicular to the outer wall surface of the second balloon, whereby the second balloon may be readily disposed within the aortic bifurcation.

Another feature of this aspect of the present invention is that a second portion of a catheter located adjacent the second end of the second balloon is disposed at an angle of approximately thirty degrees with respect to the longitudinal axis of the second balloon, whereby the second portion of the catheter may be readily disposed in an iliac artery adjacent the aortic bifurcation. A further feature of the present invention is that the second portion of the catheter may be biased into the angle of approximately thirty degrees.

The foregoing advantages are also achieved through another aspect of the present invention which is a graft for intraluminal delivery to repair a body passageway. This aspect of the present invention includes: a tube having first and second ends and a wall surface disposed between the two ends, the tube adapted to be disposed within the body passageway; and means for securing the tube within the body passageway, the securing means including a thin-walled tubular member having first and second ends and a smooth outer wall surface disposed between the first and second ends, the wall surface having a substantially uniform thickness and a plurality of slots formed therein, the slots being disposed substantially parallel to the longitudinal axis of the tubular member, the tube being secured to the outer wall surface of the tubular member; the tubular member having a first diameter which permits intraluminal delivery of the tubular member and tube into the body passageway and the tubular member and tube having a second, expanded and deformed diameter, upon the application from the interior of the tubular member of a radially, outwardly extending force, which second diameter is variable and dependent upon the amount of force applied to the tubular member, the tube and tubular member each having a predetermined length, the length of the tube and tubular member being substantially the same, whereby the tubular member may be expanded and formed to secure the tube within the body passageway.

Another feature of this aspect of the present invention is that the tube may be secured to the outer wall surface of the tubular member by a plurality of sutures. A further feature of the present invention is that at least one pair of sutures may be utilized and the sutures of each pair of sutures are disposed on the outer wall surface of the tubular member, circumferentially spaced by an angle of approximately 180 degrees. An additional feature of the present invention is that the tube may be folded and wrapped around the tubular member when the tubular member has its first diameter; and the tube unfurls and has a diameter substantially equal to the diameter of the tubular member, after the tubular member has been expanded and deformed and has the second, expanded and deformed diameter.

The aortic graft for intraluminal delivery, and method and apparatus for repairing an abdominal aortic aneurysm of the present invention, when compared to previously proposed prior art grafts and methods and apparatus for repairing aneurysms, are believed to have the advantages of: a lower mortality rate; shortened recovery periods; not requiring suturing a graft to the aorta; utilizing the existing aortic wall and thrombosis therein to support and reinforce the aortic graft; being suitable for use with patients having other chronic illnesses; and being able to be expeditiously used on an emergency basis after an aneurysm has ruptured.

While the invention will be described in connection with the preferred embodiment, it will be understood that it is not intended to limit the invention to that embodiment. On the contrary, it is intended to cover all alternatives, modifications, and equivalents, as may be included within the spirit and scope of the invention as defined by the appended claims.

DESCRIPTION OF THE INVENTION

In FIGS. 1–4 an aortic graft 150 for intraluminal delivery to repair an abdominal aortic aneurysm 151 in an aorta 152 having two iliac arteries 153L, 153R associated therewith is illustrated. Aneurysm 151 include areas of thrombosis 154, which are disposed against the interior wall surface 155 of aorta 152. Blood flows through the aorta in the direction of arrows 156. Associated with aorta 152, above aneurysm 151, are a plurality of renal arteries 157, in fluid communication with aorta 152. Aortic graft 150 is seen to generally comprise: a tube 160 having first and second ends 161, 162 and wall surface 163 disposed between the two ends, at least a portion of the tube 160 adapted to be disposed within the aneurysm 151; and means for securing 165 the first end 161 of the tube 160 to the aorta 152.

Figure 2:
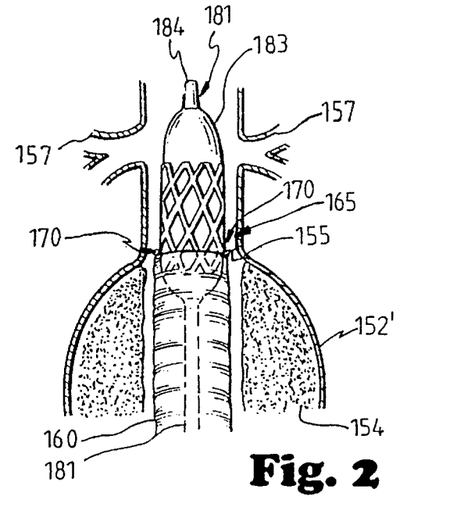
FIG. 2 is a partial cross-sectional view of a portion of the aorta of FIG. 1, illustrating the expansion of a portion of an aortic graft.
Figure 3:
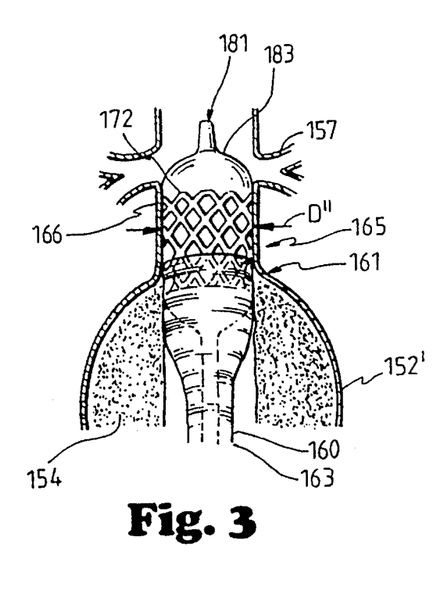
FIG. 3 is a partial cross-sectional view of the aorta of FIG. 2, illustrating the portion of the aortic graft being fully expanded.
Figure 4:
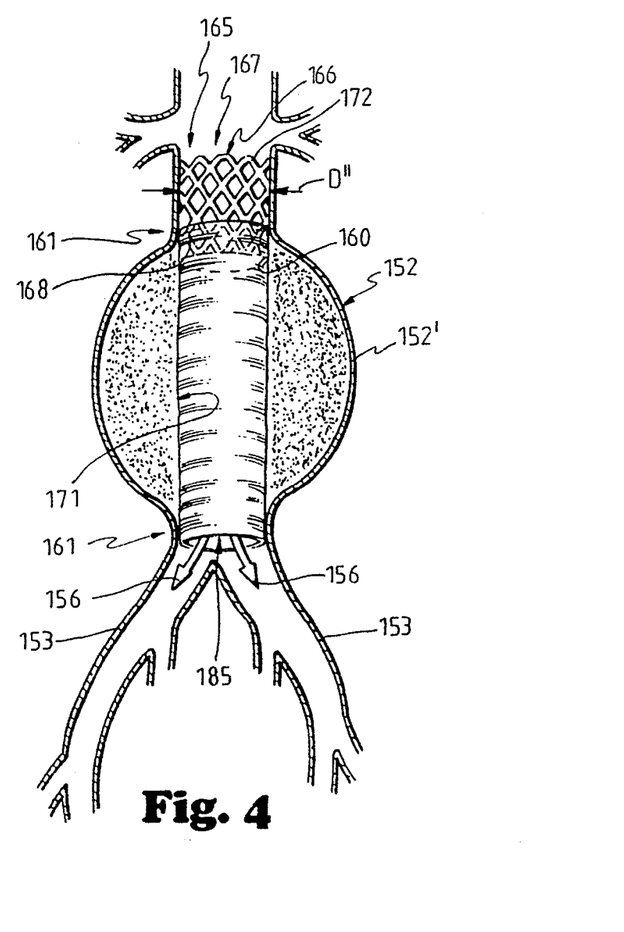
FIG. 4 is a partial cross-sectional view of an aorta with the aortic graft of the present invention having been used to repair an abdominal aortic aneurysm.

Preferably securing means 165 includes a thin-walled member 166 having first and second ends 167, 168 and a smooth outer wall surface 169 disposed between the first and second ends 167, 168 of the thin-walled member 166. The thin-walled member 166 has a first diameter D' (FIG. 1), which permits intraluminal delivery of the thin-walled member 166 into the aorta 152. Upon the application from the interior of the thin-walled member 166 of a radially, outwardly extending force, as will be hereinafter described in greater detail, the thin-walled member 166 has a second, expanded and deformed diameter D" (FIGS. 3 and 4), whereby the thin-walled member 166 is expanded and deformed to secure the first end 167 of the thin-walled member 166 and the first end 161 of the tube 160 to the aorta 152 The second diameter D" as will be hereinafter described in greater detail, is variable and dependent upon the amount of force applied to the thin-walled member 166. The first end 161 of tube 160 is connected to the second end 168 of the thin-walled member 166, as by a plurality of sutures 170 (FIG. 2). Sutures 170 may be conventional sutures of polypropylene, DACRON®, or any other suitable material. Preferably, the first end 161 of tube 160 overlaps and covers the second end 168 of thin-walled member 166, such overlap being approximately 50% of the length of thin-walled member 166. The first end 161 of tube 160, which overlaps the second end 168 of thin-walled member 166, is preferably constructed so that it is radially expandable, whereby the first end 161 of tube 160 may conform with the second, expanded and deformed diameter D" of the second end 168 of the thin-walled member 166 as seen in FIGS. 3 and 4. If tube 160 is woven, the weave of the material at its first end 161 is looser, so that the desired radial expansion can be obtained. The intermediate portion 171 of tube 160 disposed between first and second ends 161, 162 thereof, is preferably not substantially radially expandable.

Still with reference to FIGS. 1–4, thin-walled member 166 is preferably a thin-walled tubular member 172 whose wall surface 169 has a substantially uniform thickness with a plurality of slots 173 (FIGS. 1 and 5) formed therein, the slots 173 being disposed substantially parallel to the longitudinal axis of the tubular member 172. It has been found that one type of thin-walled member 166, or tubular member 172, which is particularly useful as securing means 165 are the expandable intraluminal grafts disclosed in U.S. Pat. No. 4,733,665, issued Mar. 29, 1988; U.S. Pat. No. 4,739,762, issued Apr. 26, 1988; and U.S. Pat. No. 4,776,337, issued Oct. 11, 1988, all the foregoing patents being in the name of Julio C. Palmaz, and assigned to Expandable Grafts Partnership. Each of these patents is incorporated herein by reference. Other thin-walled members 166, or tubular members 172 could be utilized as securing means 165, provided they have ability to be controllably expanded and deformed from the first diameter D', which permits intraluminal delivery of securing means 165, to the second expanded and deformed diameter D", in order to secure the thin-walled member 166, and connected tube 160 within aorta 152.

Still with reference to FIGS. 1–4, tube 160, preferably has a generally, circular cross-sectional configuration, and tube 160 may be made from a variety of materials, provided they have the requisite strength characteristics to be utilized as an aortic graft 150, as well as have the requisite compatibility with the human body in order to be used as a graft, or implant material, without being rejected by the patient's body. Examples of such materials are DACRON® and other polyester materials. TEFLON® (polytetrafluoroethylene), TEFLON® coated DACRON® material and porous polyurethane. The material can be knitted or woven, and can be warp or weft knitted. If the material is warp knitted, it may be provided with a velour, or towel like surface, which speeds up clotting of blood which contacts tube 160 in order to increase the attachment, or integration, of tube 160 to aorta 152, or to assist the integration of tube 160 to the thrombosis 154. Tube 160 can also be made of a bioerodible, or degradable material, such as albumin or collagen or a collagen coated material. A tube 160 which is bioerodable, would erode and dissolve, or degrade, over a period of time; however, it is believed that a layer of endothelium, or skin, will grow as the tube 160 erodes, the new layer of endothelium, or skin, providing a new, fluid impervious lining within aneurysm 151. As will be hereinafter described in greater detail, when aortic graft 150 is utilized in connection with an emergency insertion after a rupture of aneurysm 151, it would be preferable to make tube 160 of a fluid impervious material. Additionally, the tube 160 or securing means 160 could have a coating of a biologically inert material, such as TEFLON® or porous polyurethane.

Still with reference to FIGS. 1–4 tube 160 may have a crimped configuration to form an undulating longitudinal cross-sectional configuration (FIG. 1), whereby kinking, or twisting, or folding over upon itself will be minimized when the tube 160 is secured within the aneurysm 151, as will be hereinafter described in greater detail. This undulating configuration can be obtained by heat stamping tube 160, or in any other suitable manner, whereby the tube 160 has a "memory" and if it is twisted or kinked, it will return to its original configuration and disposition. Alternatively, tube 160 can have a smooth outer surface.

With reference to FIGS. 1–4, and FIG. 5, an apparatus 180 for repairing an abdominal aortic aneurysm 151 generally comprises: tube 160; expandable and deformable thin-walled member 166, or tubular member 172 which preferably includes slots 173 and has a smooth outer wall surface 169, the expansion and deformation of the thin-walled member 166 being controllable, as will hereinafter be described in greater detail: and a catheter 181 having an expandable, inflatable portion 182, or balloon 183 associated therewith and a nosepiece 184. The thin-walled member 166, or tubular member 172, is releasably mounted to the inflatable portion 182 of catheter 181, in any suitable fashion, whereby upon inflation of the expandable, inflatable portion 182 of catheter 181, the thin-walled member 166 is forced radially outwardly into contact with the aorta 152 to remain secured thereto, whereby the tube 160, secured to the thin-walled member 166, provides a passageway 185 (FIG. 4) through the abdominal aortic aneurysm 151, so that blood can pass through the aneurysm 151 and be separated therefrom. As seen in FIG. 4, the existing aortic wall 152' and the thrombosis 154 therein provide additional support and reinforcement for tube 160 of aortic graft 150.

Figure 1:
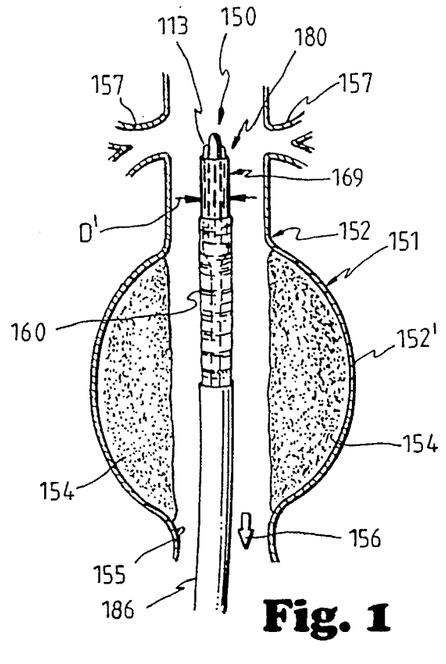
FIG. 1 is a partial cross-sectional view of an abdominal aortic aneurysm in the process of being repaired in accordance with the present invention.
Figure 5:
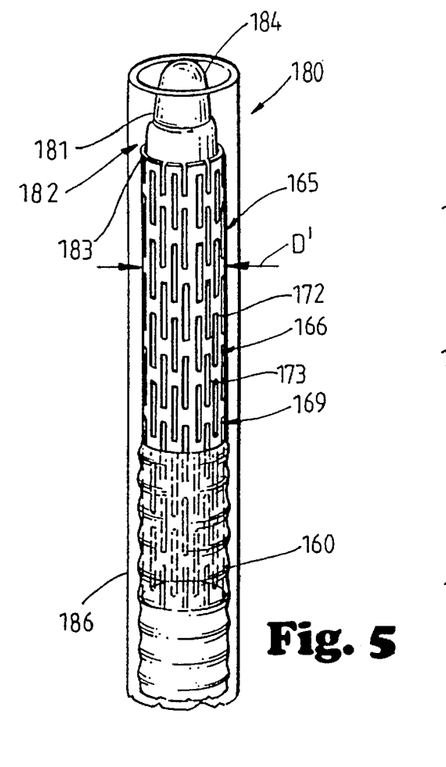
FIG. 5 is a perspective view of an apparatus for repairing an abdominal aortic aneurysm.

The apparatus 180 for repairing the abdominal aortic aneurysm 151 as illustrated in FIG. 5 is in its configuration it would have for intraluminal delivery, as also illustrated in FIG. 1. In the configuration shown in FIG. 5, the thin-walled member 166 has its first unexpanded, undeformed diameter D', and balloon 183 is shown partially inflated in FIG. 2, and completely inflated in FIG. 3. Expansion and deformation of thin-walled member 166 is controlled by the expansion of balloon 183 of catheter 181, in a conventional manner. When apparatus 180 is being intraluminally delivered, catheter 181, thin-walled member 166, and tube 160 are preferably enclosed by a conventional catheter sheath 186 which is removed, as shown in FIG. 1, as apparatus 180 is disposed in its desired location within aorta 152, as will hereinafter be described in greater detail. Deflation of balloon 183 permits the withdrawal of catheter 181 and release of the balloon 183 and catheter from aortic graft 150 after it has been disposed in the configuration shown in FIG. 4.

Figure 6:
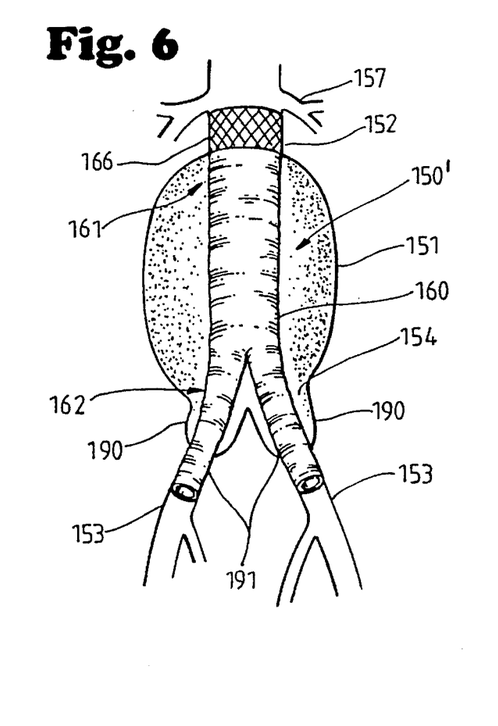
FIGS. 6–8 illustrates different embodiments of an aortic graft in accordance with the present invention, such grafts being disposed within an abdominal aortic aneurysm and/or iliac aneurysm.
Figure 8:
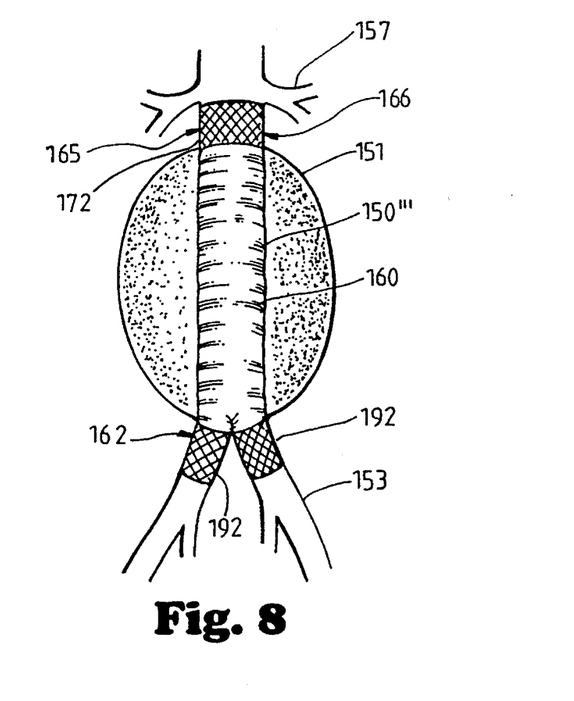
Figure 9:
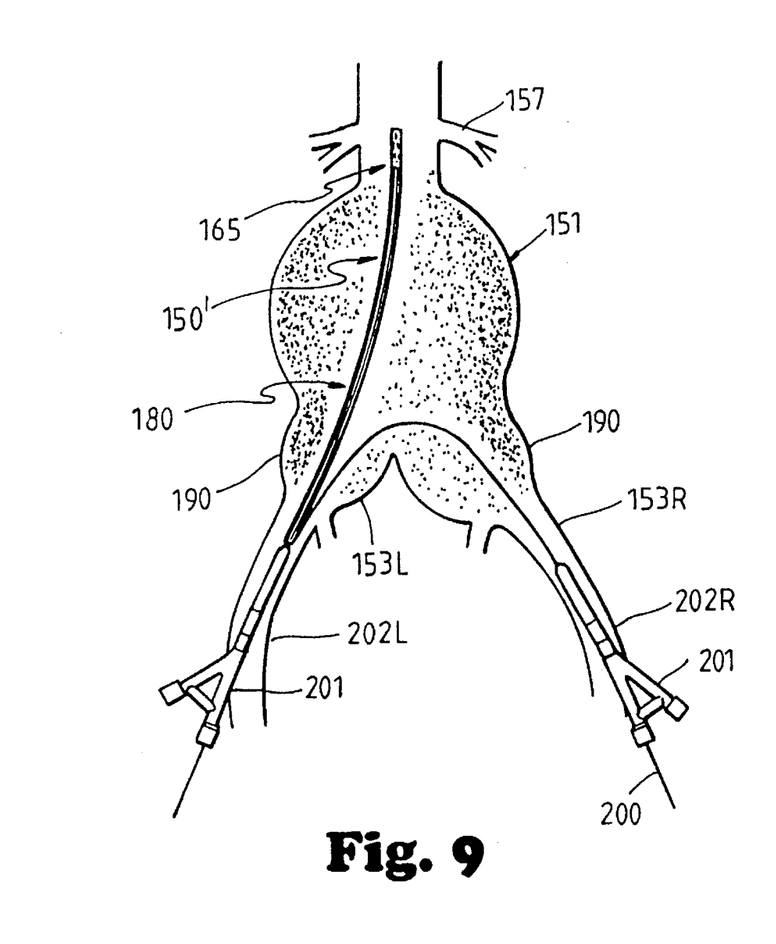
FIGS. 9–12 are partial cross-sectional views of an abdominal aortic aneurysm, illustrating one embodiment of: the method of the present invention for repairing an abdominal aortic aneurysm and iliac aneurysm.

With reference to FIGS. 6 and 8, various embodiments of grafts 150 are illustrated within aorta 152 and aneurysm 151 after aneurysm 151 has been repaired through the use of aortic graft 150 and apparatus 180. In FIG. 6, aortic graft 150' includes tube 160 as previously described, and graft 150' is secured by use of thin-walled member 166 as previously described. Abdominal aortic aneurysm 151 also includes two iliac artery aneurysms 190, which also contain the same thrombosis 154 disposed within aneurysm 151. Aortic graft 150' of FIG. 6 has the second end 162 of tube 160 bifurcated, so that two tubular passageways 191 are formed which are each in fluid communication with the first end 161 of tube 160, and the fluid passageways 191 are mated with and disposed within the two iliac arteries 153.

Figure 7:
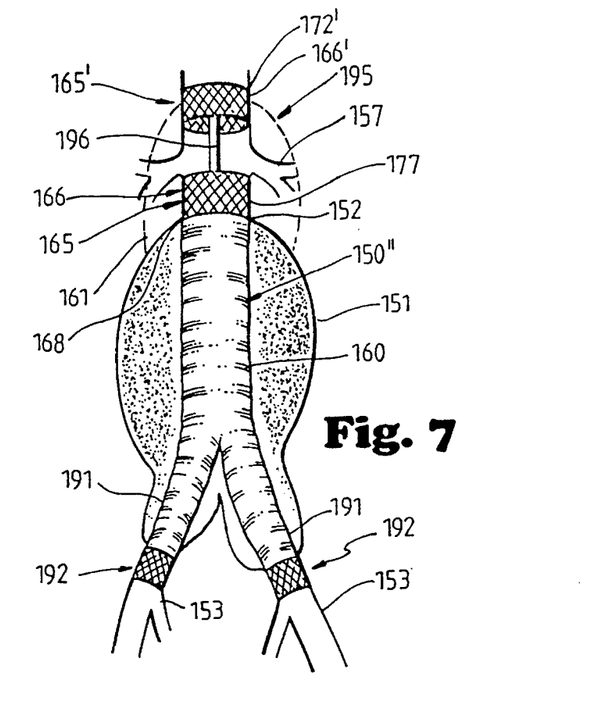

The aortic graft 150" of FIG. 7 is the same as graft 150' of FIG. 6, except that the two tubular passageways 191 include means for securing the two tubular passageways 191 to the two iliac arteries 153. Securing means 192 preferably are thin-walled members 166, or tubular members 172 of the same type of construction as those used for securing means 165. Securing means 192 may be expanded and deformed in the same manner as securing means 165 by controlled inflation of the expandable, inflatable portion 182 of catheter 181. In this regard, catheter 181 of apparatus 180 of FIG. 5 may include a second expandable, inflatable portion 182 (not shown) spaced longitudinally from the first expandable, inflatable portion 182, so that securing means 165 and 192 may be expanded and deformed simultaneously. Alternatively, apparatus 180 as shown in FIG. 5 could be utilized to first expand and deform securing means 165 disposed at the upper end 161 of tube 160, and the expandable, inflatable portion 182 could then be deflated and moved downwardly toward second securing means 192. The expandable, inflatable portion 182 would then be re-expanded and inflated to deform and expand securing means 192. Although the flow of pumped blood downwardly through aorta 152 and into iliac arteries 153 is believed to provide enough pressure to maintain passageway 191 in their desired positions, there is a slight negative vacuum pressure component associated with the pumping pressure, whereby the securing means 192 might be required. Securing means 192 also serves to insure no movement of passageways 191, caused by body movements.

In some instances, aneurysm 151 could extend above the renal arteries 157, as shown in dotted lines 195 in FIG. 7. In order to secure aortic graft 150" to repair such an aneurysm 151, 195, it is preferable to use a securing means 165' which includes first and second thin-walled members 166 and 166', or tubular members 172, 172', which are flexibly interconnected by at least one connector member 196, the first end 161 of tube 160 being . . . . secured, as previously described, to the second end 168 of thin-walled member 166 in the manner previously described. The flexible connector member 196 spans the part of the aorta 152 adjacent the renal arteries 157, so that fluid flow through renal arteries 157 is not obstructed. Preferably, two connector members 196 are utilized, the connector members being disposed 180o apart, whereby the surgeon can determine by x-ray or fluoroscopy that the two flexible connector members 196 are disposed in the position shown in FIG. 7, wherein the second connector member (not shown) is disposed directly behind the first connector member 196. If two images of connector members 196 appear on the x-ray or the fluoroscope, the surgeon will know that it is possible that one of the renal arteries 157 may be obstructed by one of the connector members 196. Securing means 165' is expanded and deformed in the same manner as previously described with respect to securing means 165.

With reference to FIG. 8, a graft 150''' is illustrated, graft 150''' being similar in design to the graft 150 illustrated in FIG. 4, with the exception that the second end 162 of tube 160 is provided with additional securing means 192 as previously described in connection with FIG. 7.

Figure 10:
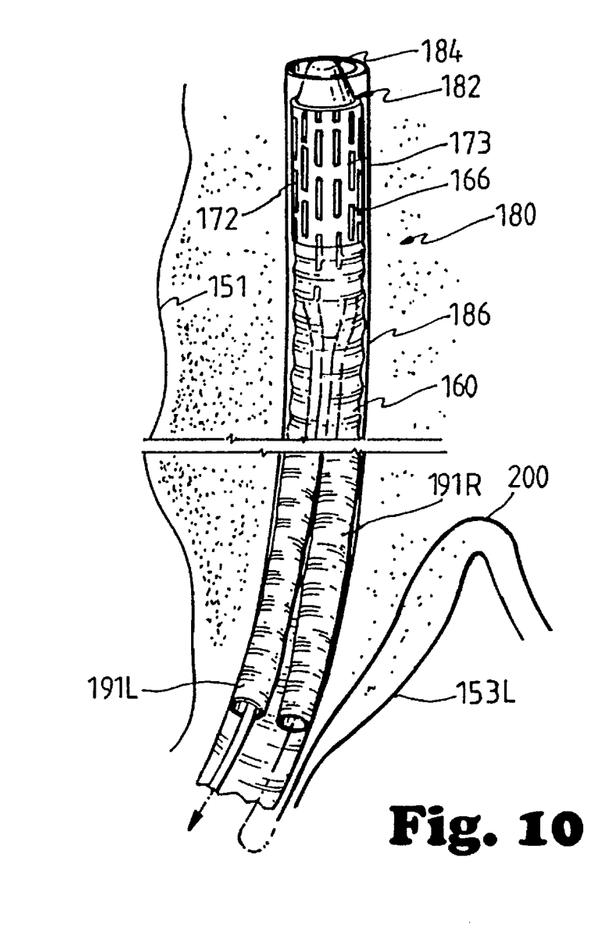
Figure 11:
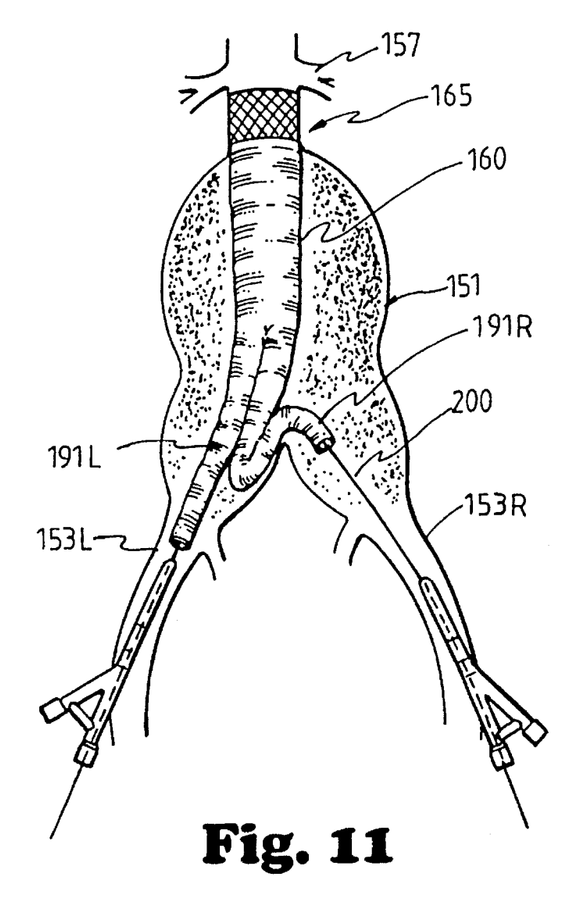
Figure 12:
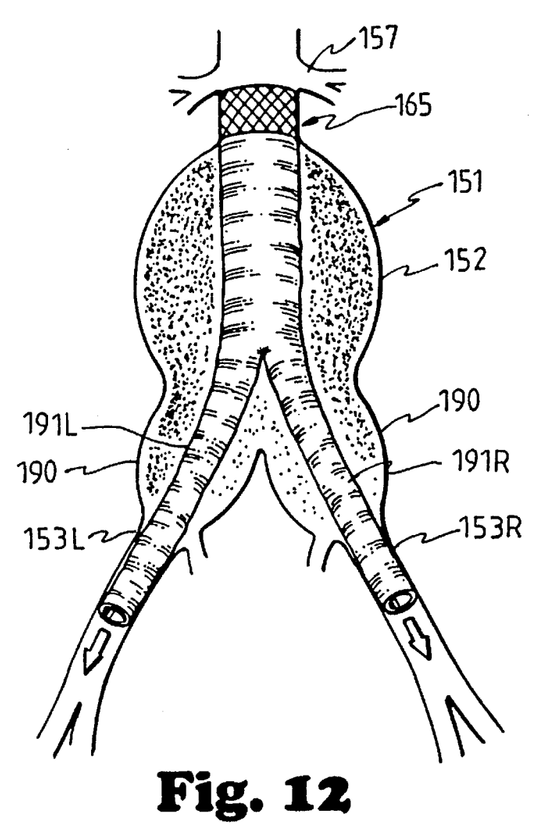

With reference to FIGS. 9–12, a method for repairing an abdominal aortic aneurysm 151 and iliac aneurysm 190 with an aortic graft 150' as illustrated in FIG. 6 will be described. After tube 160 has been connected to an expandable and deformable thin-walled member 166, or tubular member 172, as previously described in connection with FIGS. 1–5, a surgical wire 200 is introduced through a conventional catheter insertion device 201 through the right femoral artery 202R. In a conventional manner, the surgical wire 200 is passed from the right femoral artery 202R upwardly through the right iliac artery 153R through the aorta 152 and downwardly through the left iliac artery 153L and into the left femoral artery 202L and into another conventional catheter insertion device 201. Apparatus 180, including tube 160, catheter 181, and thin-walled member 166 are then intraluminally delivered into the aorta 152 and aneurysm 151, through the left femoral artery 202L, via a conventional catheter insertion device 201. Securing means 165 can be disposed in the aorta 152 in the position shown in FIGS. 9 and 1. Sheath 186 may then be removed in a conventional manner. With reference to FIGS. 10 and 11, after sheath 186 is removed, surgical wire 200 may then be sutured to the right passageway 191R of tube 160 as shown in FIG. 10. Securing means 165 may then be expanded and deformed in the manner previously described, as shown in FIG. 11. The wire 200 can then be withdrawn and pulled, so as to pull the right passageway 191R of tube 160 downwardly into the right iliac artery 153R until it assumes the position shown in FIG. 12. This same method could also be utilized to repair an aneurysm 151, including an iliac aneurysm 191 with the graft 150" of FIG. 7.

Figures 13, 13A, 14:
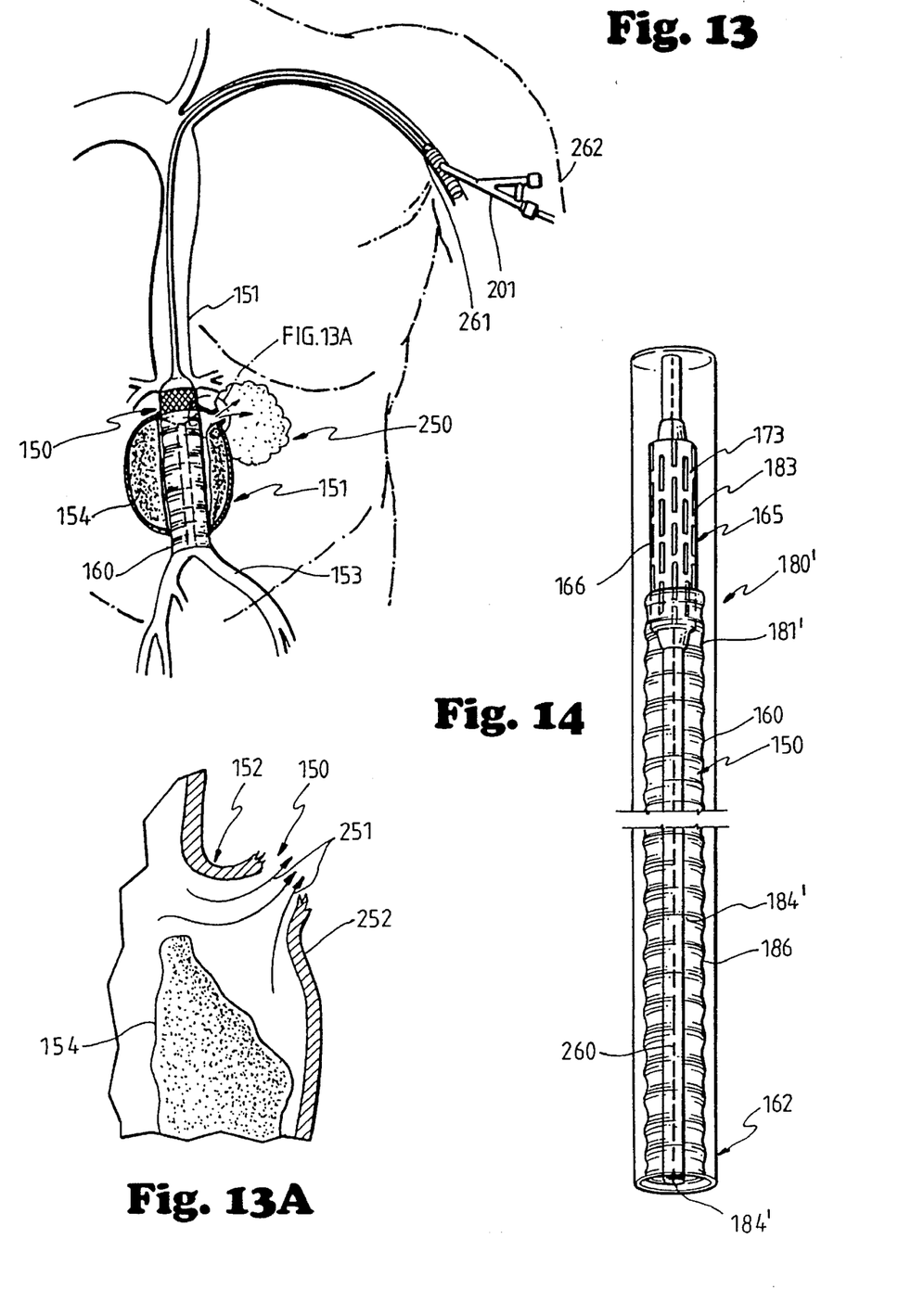
FIG. 13 is a partial cross-sectional view of a patient with a ruptured abdominal aortic aneurysm, which rupture is being repaired in accordance with the present invention.
FIG. 13a is an enlarged partial cross-sectional view of a portion of FIG. 13.
FIG. 14 is a partial cross-sectional view along the longitudinal axis of an apparatus for repairing an abdominal aortic aneurysm, after the aneurysm has ruptured.

With reference to FIGS. 13, 13a, and 14, a method and apparatus for repairing an abdominal aortic aneurysm 151 which has ruptured as shown at 250 in FIGS. 13 and 13a is illustrated. As seen in FIG. 13a, blood is illustrated by arrows 251 as flowing through the opening, or rupture, 250 in the wall 252 of aorta 152, and the thrombosis 154 is separated from wall 252. Apparatus 180', as shown in FIG. 14, is similar to apparatus 180 previously described in connection with FIG. 5. Apparatus 180' includes tube 160 of the type as previously described, a catheter 181' having an extended nosepiece 184' tube 160 being disposed about the extended nosepiece 184'. Securing means 165, as previously described, is mounted upon an expandable, inflatable portion 183 of catheter 181'. Apparatus 180' differs from that previously described, in that catheter 181' first passes through securing means 165 and then into tube 160, whereas in apparatus 180, catheter 181 first passes through tube 160 and then into securing means 165. Sheath 186 is also provided as previously described. Additionally, the second end 162 of tube 160 is restrained in the position shown in FIG. 14, as by a thread which is sutured to the lower end 162 of tube 160, the thread 260 passing through the extended catheter nosepiece 184'.

As will hereinafter be described in greater detail, it is preferable that thread 260 be able to be easily pulled through tube 160. Accordingly, it is preferred that thread 260 have a smooth, slippery surface. Nylon monofilament is thus a preferred material for thread 260.

As seen in FIG. 13, apparatus 180' is intraluminally delivered to the aorta and the ruptured aneurysm 151 through an axillary artery 261 in the patient's arm 262 whereby apparatus 180' is intraluminally delivered via the axillary artery downwardly through the aorta 152 into the position illustrated in FIGS. 13 and 1. Securing means 165 is then expanded and deformed in the manner previously described, so that aortic graft 150 assumes the configuration illustrated in FIGS. 4 and 13. In the event of a rupture 250, it is believed it would be difficult to enter the aorta 152 from the femoral artery, where as it is believed it will be readily possibly to intraluminally deliver apparatus 180' through the axillary artery 261 via usage of a conventional catheter insertion device 201. Because of the rapid flow of blood, it is preferred that the tube 160 be made fluid impervious when used for repairing aneurysms which have ruptured. It should be readily recognized that the procedure illustrated in connection with FIGS. 13, 13a, and 14 can be much more expeditiously performed then the conventional, prior art method for repairing a ruptured aneurysm 151.

Figure 15:
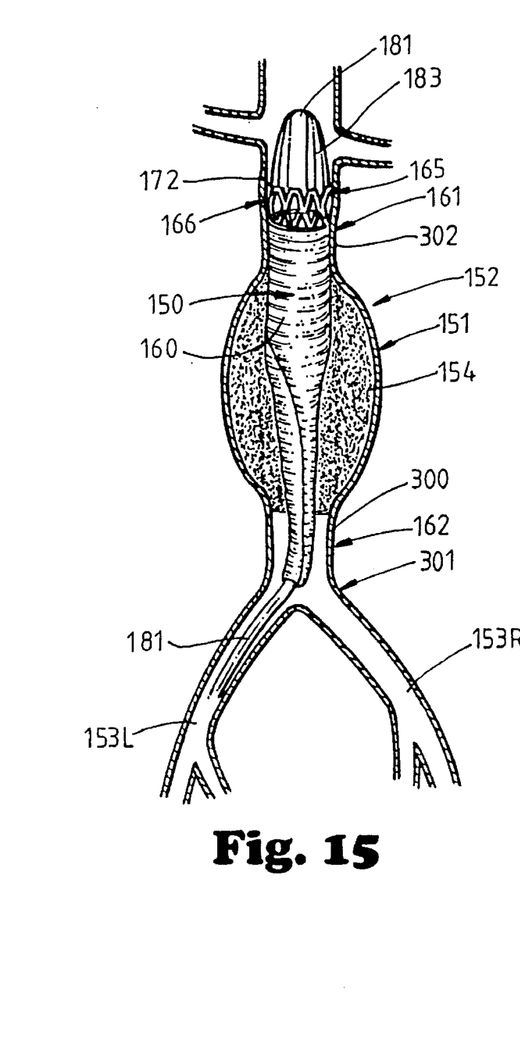
FIG. 15 is a partial cross-sectional view of the aorta of FIG. 2, illustrating the expansion of a portion of an aortic graft.
Figure 16:
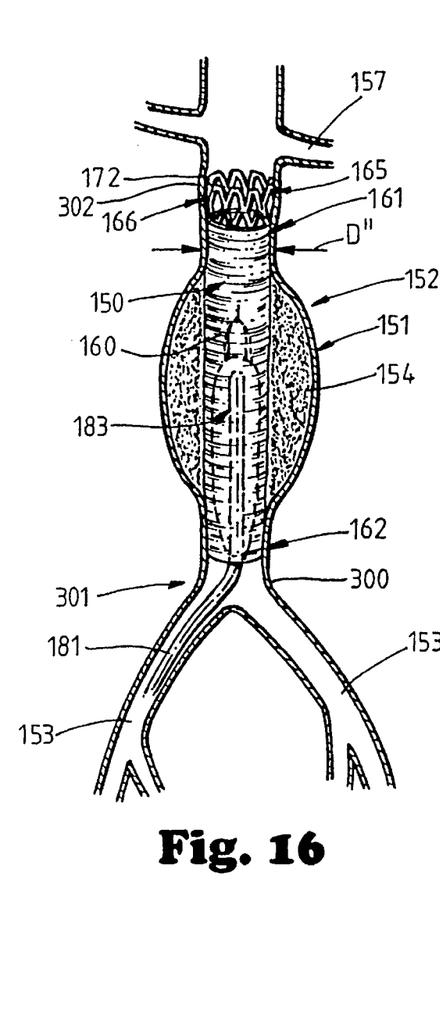
FIG. 16 is a partial cross-sectional view of the aorta of FIG. 15, illustrating the aortic graft, after it has been fully expanded.
Figure 17:
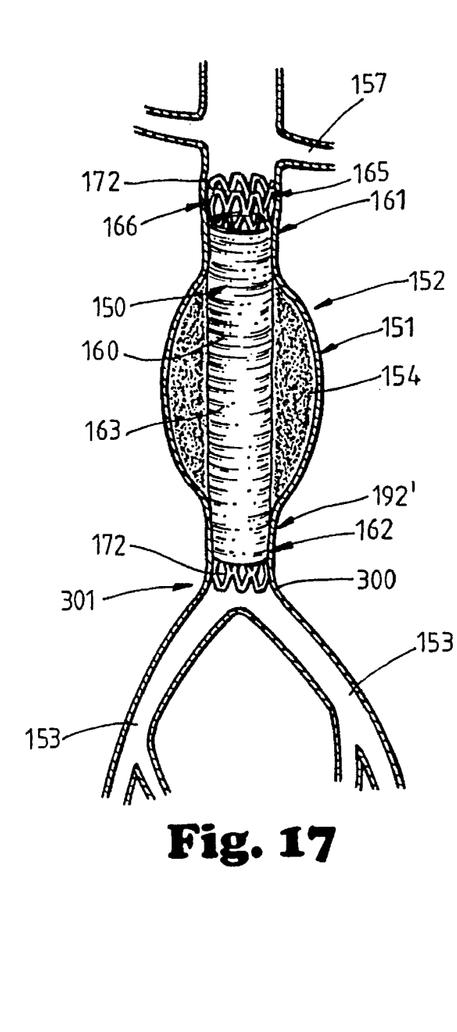
FIG. 17 is a partial cross-sectional view of the aorta of FIG. 16, having the lower end of the graft being secured within the aortic bifurcation.

With reference to FIGS. 15–17, an aortic graft 150 of the same construction as that illustrated in FIGS. 2–4, and as previously described in connection therewith, is illustrated being implanted within abdominal aortic aneurysm 151. The same reference numerals have been utilized in FIGS. 15–17 for identical elements previously described in connection with FIGS. 2–4. In FIG. 15, the securing means 165, or thin-walled member 166, which may preferably be a thin-walled tubular member 172, is being expanded and deformed by the inflation of balloon 183 of catheter 181, as previously described. After securing means 165 has been expanded and deformed to have its second expanded, and deformed, diameter D" as shown in FIG. 16, balloon 183 disposed on catheter 181 is moved downwardly through tube 160 to distend tube 160 until tube 160 has the configuration illustrated in FIGS. 4 and 16, within thrombosis 154 of abdominal aortic aneurysm 151, with the second, or lower end, 162 of tube 160 being disposed within the lower neck portion 300 of abdominal aortic aneurysm 151, or aortic bifurcation 301.

A completion aortogram may then be obtained. If the completion aortogram demonstrates reflux, or flow, back into the abdominal aortic aneurysm 151, it may be desirable to secure the second end 162 of tube 160 within the lower neck 300 of abdominal aortic aneurysm 151, or aortic bifurcation 301. Another securing means 165, or thin-walled tubular member 172, may then be intraluminally delivered to the lower end 162 of tube 160, by disposing tubular member 172 upon an expandable, inflatable portion, or balloon 183, of another catheter 181. Upon the means for securing 192' the second end 162 of tube 160, or tubular member 172, being expanded and deformed by balloon 183 of another, or second catheter 181, the means for securing 192' the second end 162 of tube 160 will be expanded within lower neck 300, or aortic bifurcation 301, into the configuration illustrated in FIG. 17.

Alternatively, aortic graft 150 may be initially provided with the means for securing 192' the second end 162 of tube 160 before the initial deployment of aortic graft 150 within abdominal aortic aneurysm 151. The second securing means 192' may be sutured to the lower end 162 of tube 160 in the same manner as securing means 165 is initially sutured to the upper end 161 of tube 160, as previously described. Second securing means 192' would likewise have a first diameter D' to permit the intraluminal delivery of tube 160 along with second securing means 192'. After securing means 165 has been expanded into its second, expanded diameter D" as shown in FIG. 16, the balloon 183 would be deflated, and catheter 181 would be moved downwardly to dispose balloon 183 within the second securing means 192'. Balloon 183 would then be reinflated to expanded second securing means 192' into the configuration illustrated in FIG. 17.

Alternatively, aortic graft 150 including first securing means 165 and second securing means 192' could be mounted upon an apparatus 180" or double balloon catheter 181" which will be hereinafter described in greater detail in connection with FIGS. 20 and 21. When using double balloon catheter 181" the first balloon 183, upon which first securing means 165 is disposed, is first inflated to secure the first end 161 of the tube 160 to the aorta. Thereafter the second balloon 183' upon which the second securing means 192' is disposed, is then inflated to expand the tubular member 172 of second securing means 192'. It should be noted that because of the shorter length of the lower neck 300 of abdominal aortic aneurysm 151, in comparison to the longer upper neck 302 of abdominal aortic aneurysm 151, the tubular member 172 of second securing means 192' is shorter in length than the tubular member 172 of the first securing means 165, to enable the second securing means 192' to be properly secured within the aortic bifurcation 301, or lower neck 300 of abdominal aortic aneurysm 151, as illustrated in FIG. 17. It should also be noted that the first securing means 165 could be any type of expandable stent, provided it has a first diameter which permits intraluminal delivery of the first securing means 165 into the aorta 152, and also has a second, expanded diameter, to secure the first end 161 of tube 160 to the aorta 152, or the upper neck 302 of abdominal aortic aneurysm 151. Preferably, the first securing means 165 is of the construction of tubular member 172 previously described, as is the construction of the second securing means 192' or the lower tubular member 172.

Figure 18:
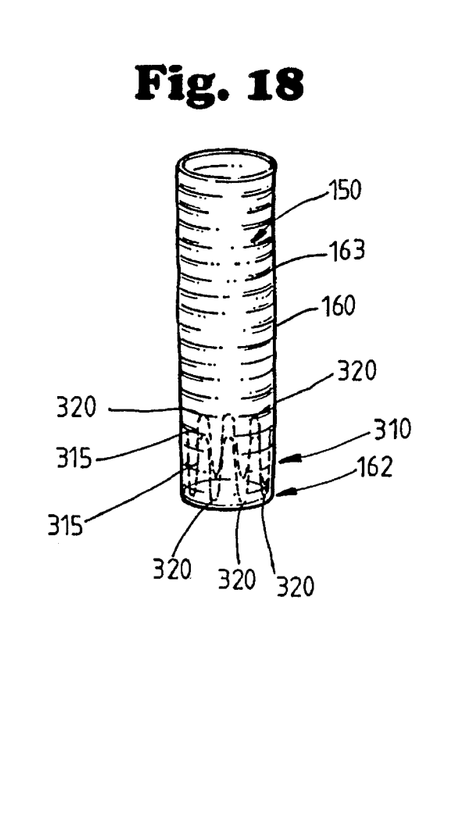
FIG. 18 is an exploded view of the lower end of an aortic graft which includes a means for sealing the lower end of the graft within the aortic bifurcation.
Figure 19:
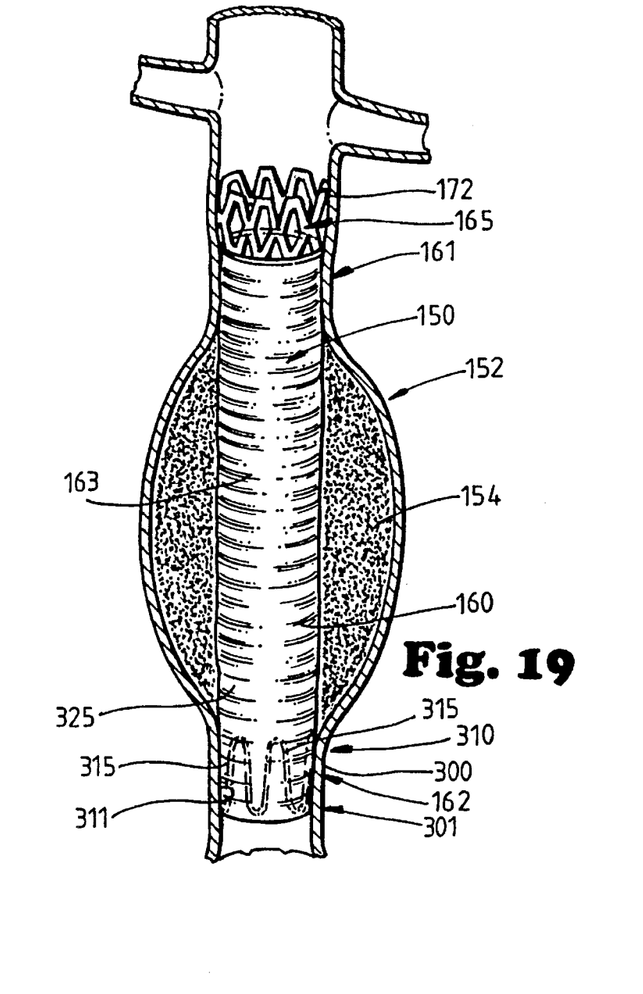
FIG. 19 is an exploded view of the lower end of the aortic graft of FIG. 18 after the graft has been expanded.

With reference to FIGS. 18 and 19, the second, or lower end 162 of tube 160 of aortic graft 150 is illustrated disposed within aortic bifurcation 301, or the lower neck 300 of abdominal aortic aneurysm 151. Aortic graft 150, instead of being provided with a means for securing 192' the second end 162 of tube 160 within aortic bifurcation 301, the second, or lower end 162, of tube 160 is provided with a means for sealing 310 the second end 162 of tube 160 within the aortic bifurcation 301, or lower neck 300 of abdominal aortic aneurysm 151.

It is very important that reflux of blood flow into the aneurysm sac, or area of thrombosis 154 in abdominal aortic aneurysm 151, be prevented by proper alignment of the tube 160 with a normal segment of the aorta, or the lower neck 300 of abdominal aortic aneurysm, at the location of the aortic bifurcation 301. It is has been determined that provided a lower neck 300 of abdominal aortic aneurysm 151 is present in a patient, and a tube 160 of adequate diameter has been tailored to a length that is appropriate to reach the lower neck 300, the undesired reflux may not occur. Based upon research, it has been determined that even if the length of the tube 160 has been calculated precisely, the anatomy of an abdominal aortic aneurysm 151 may determine whether or not high-pressure reflux of blood will occur into the aneurysm sac, or area of thrombosis 154. In general, large abdominal aortic aneurysms are less likely than small abdominal aortic aneurysms to have a lower neck 300 which has an adequate length to readily permit securing the lower end 162 of tube 160 within aortic bifurcation 301. Furthermore, the interior surface of aortic bifurcation 301 may have an irregular shape, or cross-sectional configuration, whereby it might be difficult to utilize a securing means 192' to secure the lower end 162 of tube 160 within the aortic bifurcation 301 without undesired reflux of blood flow into the aneurysm sac. Accordingly, because of the anatomy of the abdominal aortic aneurysm 151 of a patient, it would be desirable to seal the second end 162 of tube 160 within the aortic bifurcation 301, or lower neck 300 of abdominal aneurysm 151.

Preferably, sealing means 310 includes at least one wire 315 which is associated with the second end 162 of tube 160 of graft 150. The at least one wire 315 and the second end 162 of tube 160 have a first cross-sectional configuration which permits intraluminal delivery of the tube 160 and the sealing means 310 into the aortic bifurcation 301, as illustrated in FIG. 18. The at least one wire 315 and the second end 162 of tube 160 have a second end enlarged cross-sectional configuration, as illustrated in FIG. 19, wherein the at least one wire 315 in the second end 162 of tube 160 conforms to, and sealing engages, the interior surface 311 of the aortic bifurcation 301. Preferably, the at least one wire 315 is associated with the second end 162 of tube 160 by weaving the at least one wire 315 into the second end 162 of tube 160, the tube 160 being typically woven of DACRON® as previously discussed. As seen in FIGS. 18 and 19, the at least one wire 315 is woven into the second end 162 of tube 160 in a generally zigzag pattern. The at least one wire 315 may be woven into the second end 162 of tube 160 with portions 320 of the at least one wire 315 extending outwardly or inwardly of the second end 162 of tube 160, as shown in FIG. 18, as will be hereinafter described in greater detail. The at least one wire 315 may be preferably formed of gold, or tantalum, or any other suitable metallic or plastic material having the requisite flexibility and biocompatibility characteristics for the intended use of graft 150.

Still with reference to FIGS. 18 and 19, the at least one wire 315 has a thickness which permits it to be woven into the wall surface 325 of tube 160, whereby the at least one wire 315 lies in substantially the same plane as tube 160 when it has its first cross-sectional configuration, as shown in FIG. 18, which permits intraluminal delivery of the tube 160 and the at least one wire 315 into the aortic bifurcation 301. The wire 315 should be flexible and malleable, whereby upon the lower end 162 of tube 160 being expanded by a balloon 183 or 183' of a balloon catheter 181, or 181", the at least one wire 315 will be deformed into the configuration illustrated in FIG. 19, whereby the at least one wire 315 will cause the lower end 162 of tube 160 to closely conform to the interior surface 311 of aortic bifurcation 301, so as to sealingly engage the interior surface 311 of aortic bifurcation 301. The portions 320 of the at least one wire 315 which extend outwardly or inwardly of the second end 162 of tube 160, when the tube 160 and sealing means 310 have the first cross-sectional configuration illustrated in FIG. 18, permit the expansion of the lower end 162 of tube 160 into the second enlarged cross-sectional configuration illustrated in FIG. 19. If desired, as shown in FIG. 18, more than one wire 315 may be woven into the lower end 162 of tube 160 of graft 150.

Figures 20, 21:
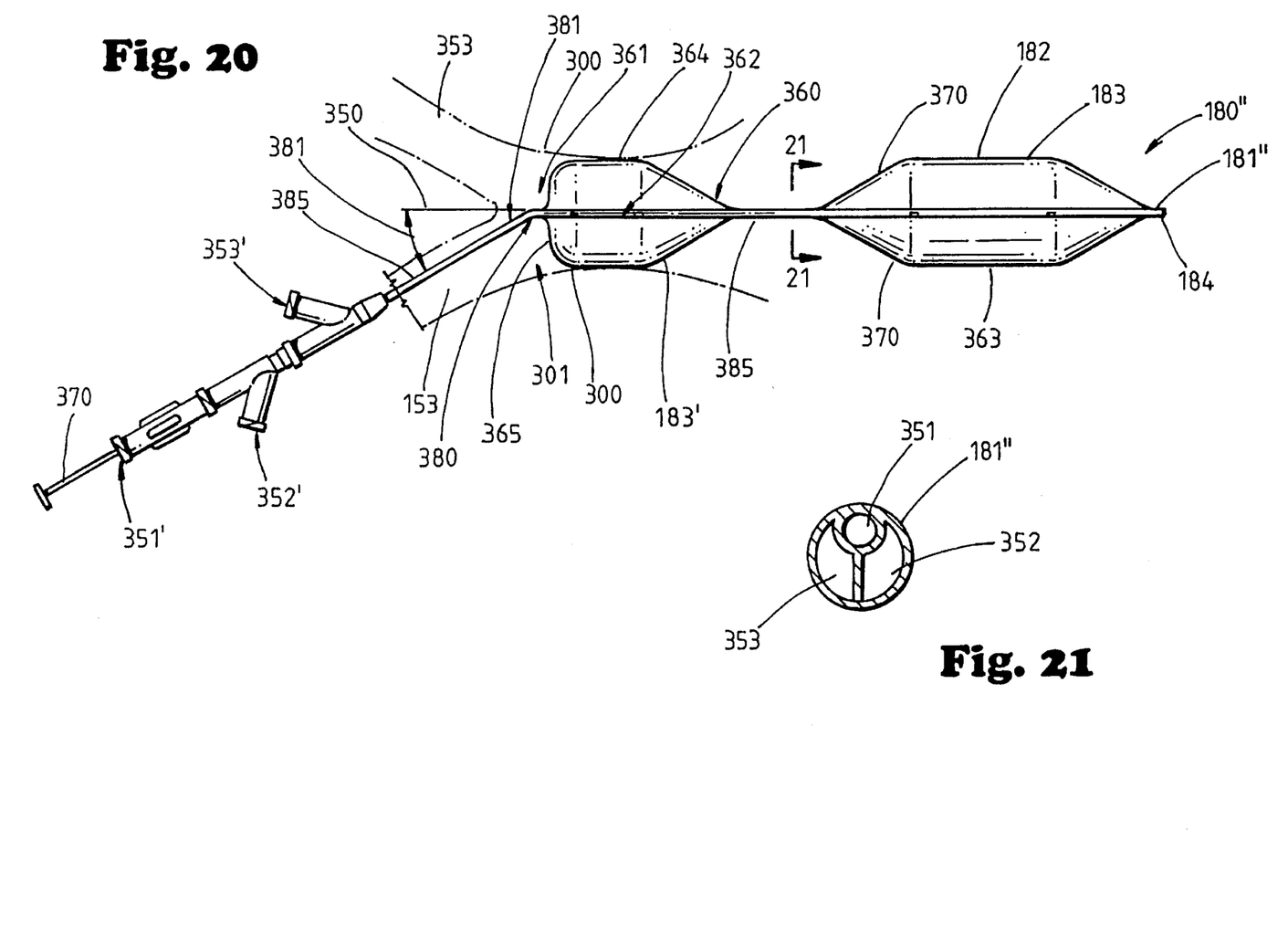
FIG. 20 is a partial cross-sectional view of a balloon device in accordance with the present invention.
FIG. 21 is a partial cross-sectional view taken along line 21—21 of FIG. 20.

With reference to FIGS. 20 and 21, a balloon device 180" for use in repairing an abdominal aortic aneurysm 151 in an aorta 152 having two iliac arteries 153 associated therewith at an aortic bifurcation 301 is shown to generally include a catheter 181" having a longitudinal axis 350 and at least three internal passageways 351, 352, 353; first and second inflatable balloons 183,183' disposed upon the catheter 181" and separated by a predetermined distance, each balloon 183, 183' connected to at least one of the internal passageways 351–353. For example, first balloon 183 may be disposed in fluid communication with internal passageway 352, which is in fluid communication with inlet port 352'; the second balloon 183' being in fluid communication with internal passageway 353 which is in fluid communication with inlet port 353'. Internal passageway 351 provides a passageway, or lumen, for a conventional guide wire (not shown) which passes through catheter 181" and can exit through a conventional nose piece 184 adjacent the first balloon 183.

With reference to FIG. 20, the second balloon 183' has first and second ends 360, 361 and a longitudinal axis 362 which is substantially parallel to the longitudinal axis 350 of catheter 181". The first end 360 of the second balloon 183' is disposed closer to the first balloon 183 than the second end 361 of the second balloon 183'. The first and second balloons 183,183', have a generally cylindrical cross-sectional configuration upon being inflated, as illustrated in FIG. 20, and this cross-sectional configuration is defined by an outer wall surface 363,364 of each balloon 183, 183'. The second end 361 of the second balloon 183' includes an end wall surface 365 which is disposed substantially perpendicular to the longitudinal axis 350 of a first portion of catheter 181" disposed within the second balloon 183' and this wall surface 365 is also substantially perpendicular to the outer wall surface 364 of the second balloon 183' when the second balloon 183' is inflated, as illustrated in FIG. 20. Because of the end wall surface 365 of the second balloon 183' being disposed substantially perpendicular to the longitudinal axis 362 of the second balloon 183', the second balloon 183' may be readily disposed, and received, within the aortic bifurcation (shown in phatom lines) 301. Were the second balloon 183' to have the conventional construction of balloon 183, including the end wall surface 370 which is not substantially perpendicular to the longitudinal axis of first balloon 183, such an end wall surface 370 would prevent the outer wall surface 364 of balloon 183' from being properly disposed within the relatively short lower neck 300 of the abdominal aortic aneurysm 151, so as to be able to properly inflate and expand either the securing means 192' of FIG. 17 or the sealing means 310 of FIG. 18, as previously described.

Still with reference to FIG. 20, a second portion 380 of catheter 181" located immediately adjacent the second end 361 of the second balloon 183', is disposed at an angle 381 of approximately thirty degrees with respect to the longitudinal axis 362 of the second balloon 183'. The second portion 380 of the catheter 181" may thus be readily disposed in an iliac artery 153 of the aortic bifurcation 301, which further assists the proper deployment of second balloon 183' within the lower neck 300 of abdominal aortic aneurysm 151, or aortic bifurcation 301, so that it may properly be inflated to expand securing means 192' or sealing means 310, as previously described. The second portion 380 of catheter 181" may be biased into the angle 381 of approximately thirty degrees, such a by molding catheter 181" with the angle 381 of second portion 380 being formed by the molding process. If catheter 181" is formed of an extended plastic, the angulated second portion 380 can be formed by heating the second portion and then bending it to have the desired angular configuration. The desired angular configuration will then be "heat set" after the plastic material cools.

A stiff guide wire (not shown), or mandrel 370, which enters catheter 181' at inlet port 351 of internal passageway 351 could serve to provide catheter 181" with the desired relatively straight orientation of catheter 181" during deployment of apparatus 180" into the abdominal aortic aneurysm 151, and upon withdrawal of the guide wire, or mandrel 370 the second portion 380 of catheter 180" would be biased into the configuration illustrated in FIG. 20. Alternatively, the second portion 380 of catheter 181" may be more flexible than the other, or first, portions 385 of catheter 181", which permits the second portion 380 to be readily angularly disposed at the desired angle of approximately thirty degrees with respect to the longitudinal axis 362 of the second balloon 183'. Such increased flexibility may be provided by forming the second portion 380 of catheter 181" with a wall thickness which is thinner than the wall thickness of the other, or first portions, 385 of the catheter 181", whereby the second portion 380 is more flexible than the first portions 385. Alternatively, the second portion 380 may be formed of a first material and the other portions 385 of the catheter 181" are formed of a second material, the first material being more flexible than the second material.

In use, the balloon device, or apparatus, 181" would initially have the balloons 183, 183' uninflated, with the balloons disposed with respect to catheter 181" in a conventional manner to permit intraluminal delivery of apparatus 180". A securing means 165, as previously discussed, in connection with FIGS. 1–5 and 15–17 would be associated with first balloon 183, and either a securing means 192' of FIG. 17, or a sealing means 310 of FIG. 18, would be associated with the second balloon 183'. As previously described, a sheath 186 (FIG. 5) would be disposed about apparatus 180", the sheath 186 being withdrawn as illustrated in FIG. 1. The first balloon 183 would be inflated as previously described to expand securing means 165, and the second balloon 183' would be inflated to expand securing means 192' or sealing means 310, as previously described With reference to FIGS. 22–24, a graft 400 for intraluminal delivery to repair a body passageway (not shown) generally includes a tube 160 having first and second ends 161, 162 and a wall surface 163 disposed between the two ends 161, 162, the tube 160 adapted to be disposed within the body passageway; and a means for securing 410 the tube 160 within the body passageway. Tube 160 is of the same construction as tube 160 previously described in connection with FIGS. 1–5, with the exception that if tube 160 is woven, the weave of the material is preferably the same throughout, so that upon radial expansion of securing means 410 from the configuration illustrated in FIG. 22 to the enlarged configuration illustrated in FIG. 23, the tube 160 will have substantially the same cross-sectional configuration throughout its length. The tube 160 may be woven so as to be radially expandable, or it may be woven so that it is not substantially radially expandable, in which case the diameter of the graft 400, as shown in FIG. 23, is determined by the diameter of the tube when it is initially woven into tube 160.

Figure 22:
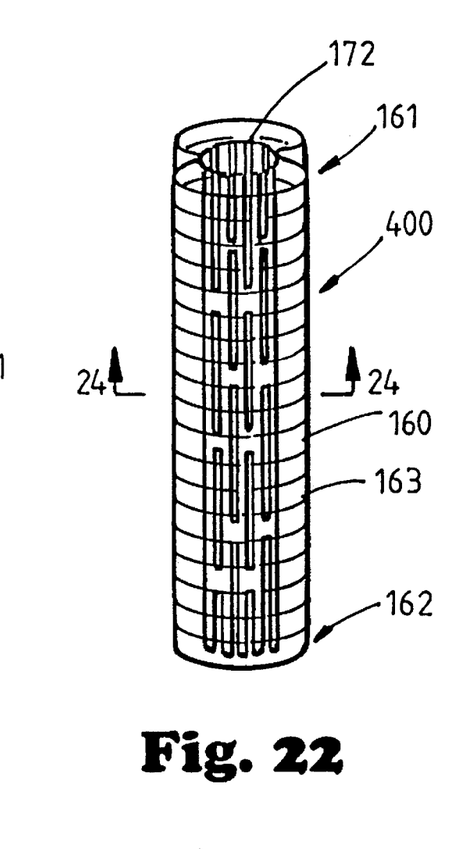
FIG. 22 is a perspective view of a graft for a body passageway.

The construction of securing means 410 is identical to that of securing means 165, or tubular member 172, previously described in connection with FIGS. 1–5, with the exception that the tube 160 and tubular member 172 have a predetermined length, the length of the tube 160 and tubular member 172 being substantially the same. Tube 160 is secured to the outer wall surface 169 of the tubular member 172 by a plurality of sutures 401. Preferably, at least one pair of sutures 401 are utilized and the sutures 401 of each pair of sutures are disposed on the outer wall surface 169 of tubular member 172, circumferentially spaced by an angle of approximately 180 degrees, as shown in FIG. 24. Tube 160 is folded and wrapped around the tubular member 172 when the tubular member has its first unexpanded diameter, as illustrated in FIG. 24, the tube 160 being folded and wrapped around the tubular member 172 in the direction of arrows 402, in a manner similar to the manner in which balloons, such as balloons 183, 183', are initially disposed upon a catheter, such as catheter 181". A conventional catheter (not shown) having a expandable, inflatable portion, such as a balloon, (not shown) is passed through tubular member 172, and a conventional sheath (not shown) is disposed over the graft 400 which is mounted upon the balloon of a catheter.

After the graft 400 has been intraluminally delivered to the desired location within a body passageway, the sheath is withdrawn in a conventional manner, and the balloon is expanded to expand and deform tubular member 172, as previously described. Upon the expansion of tubular member 172, the tube 160 unfurls and after tubular member 172 has been expanded to its desired diameter, the tube has a diameter substantially equal to the diameter of tubular member 172, as shown in FIG. 123.

Figure 23:
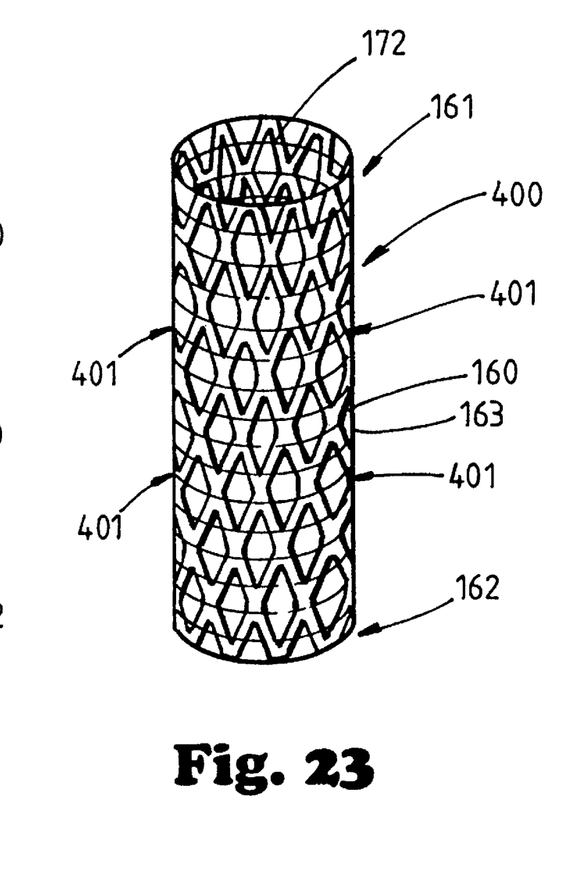
FIG. 23 is a perspective view of the graft of FIG. 22 in its fully expanded configuration.
Figure 24:
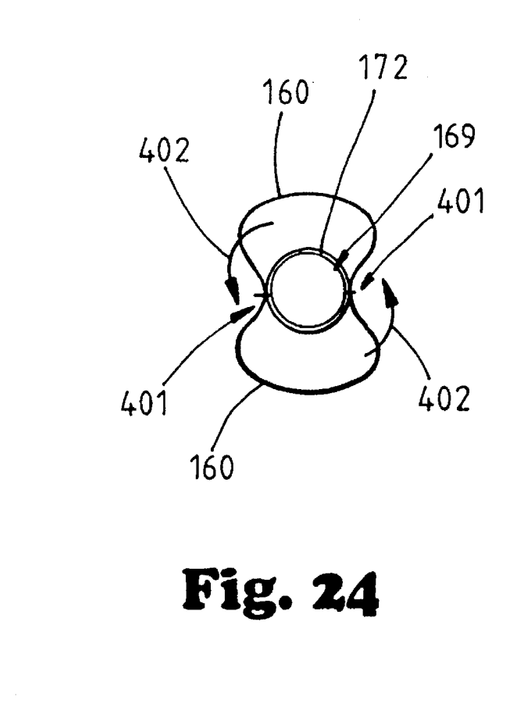
FIG. 24 is a partial cross-sectional view taken along line 24—24 of FIG. 22.

The graft 400 of FIGS. 22–24 is believed to be useful to repair abdominal aortic aneurysms, when the abdominal aortic aneurysm has a length shorter than that illustrated in FIGS. 15–17, or may be used to repair other aneurysms having a relatively short length. It is believed that the graft 400 may also be useful in connection with the treatment of arterial venous fistulas, false aneurysms, dissection procedures, and trauma-injury of arteries.

It is to be understood that the invention is not limited to the exact details of construction, operation, exact materials or embodiments shown and described, as obvious modifications and equivalents will be apparent to one skilled in the art. For example, the balloon device could be provided with only the second balloon, the first balloon being deleted. Additionally, the wall surface of the thin-walled member could be formed by a plurality of wires having a smooth exterior surface. Accordingly, the invention is therefore to be limited only by the scope of the appended claims.

I claim:

1. An aortic graft for intraluminal delivery to repair an abdominal aortic aneurysm in an aorta having two iliac arteries associated therewith at an aortic bifurcation, comprising:

a tube having first and second ends, an intermediate portion disposed between the first and second ends, and a wall surface disposed between the two ends, at least a portion of the tube adapted to be disposed within the abdominal aortic aneurysm, the intermediate portion of the tube being not substantially radially expandable, and the first end of the tube being radially expandable;

a first means for securing the first end of the tube to the aorta, the first securing means having a first diameter which permits intraluminal delivery of the first securing means into the aorta and the first securing means having a second, expanded diameter, to secure the first end of the tube to the aorta; and a second means for securing the second end of the tube at the aortic bifurcation, the second means for securing being disposed at the second end of the tube.

2. The aortic graft of claim 1, wherein the second means for securing the second end includes a thin-walled tubular member having a longitudinal axis, an interior, first and second ends and a smooth outer tubular member wall surface disposed between the first and second ends, the tubular member wall surface having a substantially uniform thickness and a plurality of slots formed therein, the slots being disposed substantially parallel to the longitudinal axis of the tubular member, the second end of the tube being secured to the first end of the tubular member; the tubular member having a first diameter which permits intraluminal delivery of the tubular member into the aorta and the tubular member having a second, expanded and deformed diameter, upon an application from the interior of the tubular member of a radially, outwardly extending force, which second diameter is variable and dependent upon the force applied to the tubular member, whereby the tubular member may be expanded and deformed to secure the second end of the tubular member within the aortic bifurcation.

3. The aortic graft of claim 2, wherein the second end of the tube is secured to the first end of the tubular member by a plurality of sutures.

4. The aortic graft of claim 1, wherein the tube is crimped to form an undulating longitudinal cross-sectional configuration, whereby kinking or twisting of the tube is minimized.

5. An aortic graft for intraluminal delivery to repair an abdominal aortic aneurysm in an aorta having two iliac arteries associated therewith at an aortic bifurcation, comprising:

a tube having first and second ends and a wall surface disposed between the two ends, at least a portion of the tube adapted to be disposed within the abdominal aortic aneurysm;

a first means for securing the first end of the tube to the aorta, the first securing means having first and second ends and a first diameter which permits intraluminal delivery of the first securing means into the aorta and the first securing means having a second, expanded diameter, to secure the first end of the tube to the aorta; and a second means for securing the second end of the tube at the aortic bifurcation, the second means for securing being disposed at the second end of the tube and having first and second ends;

the first means for securing being a first tubular member, the second end of the first tubular member being disposed within the first end of the tube, with the first end of the first tubular member being disposed outside the first end of the tube, the first end of the first tubular member being adapted to directly contact the aorta; and the second means for securing being a second tubular member, the first end of second tubular member being disposed within the second end of the tube, with the second end of the second tubular member being disposed outside the second end of the tube, the second end of the second tubular member being adapted to directly contact the aortic bifurcation.

6. The aortic graft of claim 5, wherein the second tubular member has a longitudinal axis, an interior, and a smooth outer tubular member wall surface disposed between the first and second ends, the tubular member wall surface having a substantially uniform thickness and a plurality of slots formed therein, the slots being disposed substantially parallel to the longitudinal axis of the tubular member, the tubular member having a first diameter which permits intraluminal delivery of the tubular member into the aorta and the tubular member having a second, expanded and deformed diameter, upon an application from the interior of the tubular member of a radially, outwardly extending force, which second diameter is variable and dependent upon the force applied to the tubular member, whereby the tubular member may be expanded and deformed to secure the second end of the tubular member within the aortic bifurcation.

7. The aortic graft of claim 6, wherein the second end of the tube is secured to the first end of the tubular member by a plurality of sutures.

8. The aortic graft of claim 5, wherein the tube has an intermediate portion which is not substantially radially expandable.

9. The aortic graft of claim 5, wherein the tube is crimped to form an undulating longitudinal cross-sectional configuration, whereby kinking or twisting of the tube is minimized.

* * * * *